United States Patent
Coutinho et al.

(10) Patent No.: US 10,315,986 B1
(45) Date of Patent: Jun. 11, 2019

(54) SYSTEMS AND METHODS FOR FORMING A SOLUTION OF AMMONIUM CARBAMATE

(71) Applicant: SOLENIS TECHNOLOGIES, L.P., Wilmington, DE (US)

(72) Inventors: Cecil Coutinho, Wilmington, DE (US); Michael Mitchell, Wilmington, DE (US); Stephen Vinciguerra, Wilmington, DE (US)

(73) Assignee: SOLENIS TECHNOLOGIES, L.P., Wilmington, DE (US)

( * ) Notice: Subject to any disclaimer, the term of this patent is extended or adjusted under 35 U.S.C. 154(b) by 0 days.

(21) Appl. No.: 15/947,182

(22) Filed: Apr. 6, 2018

(51) Int. Cl.
| | | |
|---|---|---|
| *C07C 269/04* | (2006.01) |
| *C07C 271/02* | (2006.01) |
| *B01F 3/04* | (2006.01) |
| *B01J 23/04* | (2006.01) |
| *B01D 53/58* | (2006.01) |
| *B01D 53/62* | (2006.01) |

(52) U.S. Cl.
CPC ............ *C07C 269/04* (2013.01); *B01D 53/58* (2013.01); *B01D 53/62* (2013.01); *B01F 3/04106* (2013.01); *B01J 23/04* (2013.01); *C07C 271/02* (2013.01); *B01D 2251/304* (2013.01); *B01D 2251/604* (2013.01); *B01D 2251/80* (2013.01); *B01F 2201/01* (2013.01)

(58) Field of Classification Search
CPC ..... C07C 269/04; C07C 271/02; B01D 53/62; B01D 53/58; B01D 2251/80; B01D 2251/304; B01D 2251/604; B01J 23/04; B01F 3/04106; B01F 2201/01
See application file for complete search history.

(56) References Cited

FOREIGN PATENT DOCUMENTS

CN          203803478       *   9/2014

OTHER PUBLICATIONS

Kumar, Parul (Drug Production in Cell Cultures and Bioreactor, pp. 1-12, published Oct. 2015) (Year: 2015).*
CN203803478 translated (Year: 2014).*

* cited by examiner

*Primary Examiner* — Yevgeny Valenrod
*Assistant Examiner* — Blaine G Doletski
(74) *Attorney, Agent, or Firm* — Lorenz & Kopf, LLP

(57) ABSTRACT

A method for forming a solution of ammonium carbamate is provided herein. The method includes, but is not limited to, providing a reactor comprising a solution of ammonia. The method further includes, but is not limited to, feeding carbon dioxide through the solution of ammonia to form a mixture. The method further includes, but is not limited to, combining a solution of sodium hydroxide and the mixture to form the ammonium carbamate.

12 Claims, 4 Drawing Sheets

SYSTEMS AND METHODS FOR FORMING A SOLUTION OF AMMONIUM CARBAMATE

TECHNICAL FIELD

The present disclosure generally relates to systems and methods for forming ammonium carbamate and more particularly relates to systems and methods for forming aqueous solutions of ammonium carbamate.

BACKGROUND

Conventional systems and methods for forming ammonium carbamate rely on the reaction of gaseous mixtures of ammonia, water, and carbon dioxide to form solid ammonium carbamate. One conventional system and method for forming ammonium carbamate utilizes a synthesis reaction bag and introducing the gases ammonia and carbon dioxide at opposite ends of the reaction bag. As the gases of ammonia and carbon dioxide disperse through the reaction bag, reaction of the gases proceeds upon contact of the gases to one another to form the solid ammonium carbamate. The solid ammonium carbamate is then removed from the synthesis reaction bag and provided to users as a solid raw material. The users may then form aqueous solutions of ammonium carbamate from the solid ammonium carbamate for use in various industrial, commercial, and agricultural applications, such as biocides and fertilizer.

The use of solid ammonium carbamate poses several challenges related to quality and handling. During transport of the solid ammonium carbamate, the solid ammonium carbamate is in equilibrium with its atmosphere resulting in partial decomposition of the ammonium carbamate depending on transport duration and temperature. The purity of solid ammonium carbamate can vary, thereby impacting the quality of the aqueous solution formed therefrom. The solid ammonium carbamate off-gases ammonia during handling when processing into an aqueous solution, thereby requiring environmental controls to reduce exposure to workers.

Accordingly, it is desirable to provide systems and methods for forming ammonium carbamate. Furthermore, other desirable features and characteristics will become apparent from the subsequent summary and detailed description and the appended claims, taken in conjunction with the accompanying drawings and the foregoing technical field and background.

BRIEF SUMMARY

Various non-limiting embodiments of solutions of ammonium carbamate, and various non-limiting embodiments of systems and methods for the same, are disclosed herein.

In a non-limiting embodiment, a method for forming a speciated solution of ammonium carbamate is provided herein. The method includes, but is not limited to, providing a reactor comprising a solution of ammonia. The method further includes, but is not limited to, feeding carbon dioxide through the solution of ammonia to form a mixture. The method further includes, but is not limited to, combining a solution of sodium hydroxide and the mixture to form ammonium carbamate.

In a non-limiting embodiment, a system for forming a speciated solution of ammonium carbamate is provided herein. The system includes, but is not limited to, a reactor defining an interior. The reactor includes, but is not limited to, a feed line disposed within the interior. The feed line includes, but is not limited to, an inlet and an outlet with the inlet in fluid communication with the outlet. The outlet is disposed within the interior of the reactor. The system further includes, but is not limited to, a solution of ammonia disposed in the interior. The system further includes, but is not limited to, a carbon dioxide source including, but not limited to, carbon dioxide and in fluid communication with the inlet. The system further includes, but is not limited to, a sodium hydroxide source including, but not limited to, sodium hydroxide and in fluid communication with the reactor. The feed line is configured to receive the carbon dioxide from the carbon dioxide source at the inlet and release the carbon dioxide through the outlet. The carbon dioxide released through the outlet is configured to feed through the solution of ammonia during formation of the ammonium carbamate solution.

BRIEF DESCRIPTION OF THE DRAWINGS

Other advantages of the disclosed subject matter will be readily appreciated, as the same becomes better understood by reference to the following detailed description when considered in connection with the accompanying drawings wherein.

DETAILED DESCRIPTION

Figure 1:
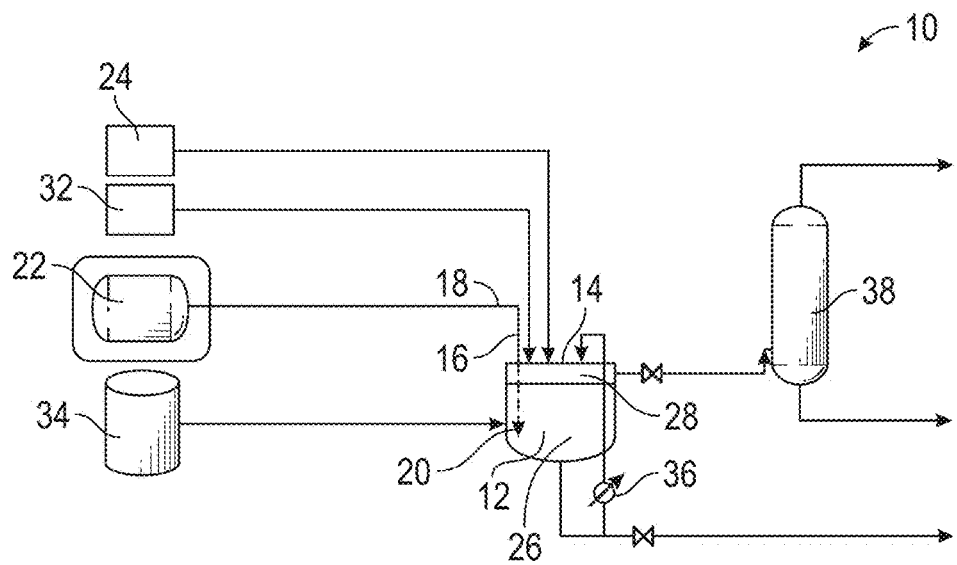
FIG. 1 is a flow chart illustrating a non-limiting embodiment of a system for forming ammonium carbamate.

The following detailed description is merely exemplary in nature and is not intended to limit the systems and methods as described herein. Furthermore, there is no intention to be bound by any theory presented in the preceding background or the following detailed description.

A speciated solution of ammonium carbamate is provided herein. The speciated solution of ammonium carbamate includes the reaction product of a solution of ammonia, carbon dioxide, and a solution of sodium hydroxide. In certain embodiments, the solution of ammonia and the carbon dioxide are reacted to form a mixture. In these embodiments, the mixture may be combined with the solution of sodium hydroxide to form the ammonium carbamate. In these embodiments, the order of addition of the solution of ammonia, the carbon dioxide, and the solution of sodium hydroxide may improve the reaction efficiency of forming the ammonium carbamate. As one example, if the carbon dioxide was charged to the water in the absence of ammonia, the carbon dioxide would not solubilize in the water due to its low solubility in water. As another example, if the ammonia and sodium hydroxide were first combined to form a solution, the higher pH and the temperature rise of the solution may cause off-gassing of ammonia. Additionally, the carbon dioxide charged to this ammonia/sodium hydroxide solution would lead to precipitation of carbonate salts.

A method for forming ammonium carbamate is also provided herein. The method may be a semi-batch or a continuous process. In a semi-batch process, a fixed volume and concentration of ammonia may be combined with carbon dioxide and sodium hydroxide. In a continuous process, ammonia, carbon dioxide, and sodium hydroxide are combined at a controlled flow rate. The method below will describe the detailed method for a semi-batch process; however, one skilled in the art could easily convert this method to one or more continuous processes.

Starting with the raw materials used to make ammonium carbamate, and making a speciated solution from these materials, requires fewer synthesis steps as compared to conventional methods. Further, the gas-liquid reaction of the present disclosure is less exothermic than conventional methods such that the heat of reaction can be more easily removed. Moreover, this gas-liquid reaction can be carried out in conventional reactor equipment and eliminates the need to handle solids. A number of equilibrium reactions, shown below, describe the speciation of solutions of ammonium carbamate into other species such as ammonium bicarbonate, so that beginning with carbamate solid does not result in a solution differentiated from a solution made from appropriate amounts of ammonia and carbon dioxide.

$$2NH_{3(aq)} + CO_{2(g)} \leftrightarrow NH_2COONH_{4(aq)}$$

$$2NH_4HCO_{3(aq)} \leftrightarrow (NH_4)_2CO_{3(aq)} + CO_{2(g)} + H_2O$$

$$NH_4HCO_{3(aq)} \leftrightarrow NH_{3(aq)} + CO_{2(g)} + H_2O$$

$$(NH_4)_2CO_{3(aq)} \leftrightarrow 2NH_{3(aq)} + CO_{2(g)} + H_2O$$

$$NH_2COONH_{4(aq)} + H_2O \leftrightarrow NH_4HCO_{3(aq)} + NH_{3(aq)}$$

With reference to FIG. 1 (shown as a semi-batch process utilizing a system 10), the method includes the steps of providing a reactor 12 including the solution of ammonia. The solution of ammonia may include ammonia and a solvent, such as water. The solution of ammonia may include ammonia in an amount of at least about 5 wt. %, alternatively at least about 7 wt. %, or alternatively at least about 10 wt. %, based on a total weight of the solution of ammonia. The solution of ammonia may include ammonia in an amount of from about 5 to about 50 wt. %, alternatively from about 7 to about 40 wt. %, or alternatively from about 10 to about 30 wt. %, based on a total weight of the solution of ammonia. In embodiments, the solution of ammonia is an aqueous solution including water in an amount of from about 50 to about 95 wt. %, alternatively from about 60 to about 93 wt. %, or alternatively from about 70 to about 90 wt. %, based on a total weight of the solution of ammonia.

The method further includes the step of feeding carbon dioxide through the solution of ammonia to form the mixture. The solution of ammonia refers to the solution of ammonia including at least about 1 wt. %, alternatively at least about 5 wt. %, alternatively at least about 10 wt. %, alternatively at least about 15 wt. %, or alternatively at least about 25 wt. % based on a total weight of the solution of ammonia. As will be described in greater detail below, carbon dioxide is introduced into the reactor 12 exhibiting improved interfacial contact with the solution of ammonia. In embodiments, the carbon dioxide is fed through the solution of ammonia to an NH$_3$/CO$_2$ molar ratio of from about 1.6 to about 2.1, alternatively from about 1.8 to about 2.1, or alternatively from about 2.0 to about 2.1. In embodiments, feeding of carbon dioxide into the reactor 12 is halted upon reaching the desired molar ratio. In embodiments employing the semi-batch process, the step of feeding carbon dioxide is performed as quickly as is permitted by heat and mass transfer limitations of the system.

In embodiments, the step of feeding carbon dioxide is defined as feeding a plurality of bubbles of gaseous carbon dioxide through the solution of ammonia to form the mixture. It is to be appreciated that the plurality of bubbles of gaseous carbon dioxide may only feed through a portion of the solution of ammonia and still be considered to feed through the solution of ammonia. The method may further include the step of forming the plurality of bubbles having a small enough diameter, using an appropriate combination of sparger orifice/pore size and agitation conditions. In one embodiment, sufficiently small bubbles were generated with a porous sparge element whose pore size varied between 2 and 10 microns. The plurality of bubbles may have a surface area to volume ratio of at least about 8100 m$^2$/m$^3$. The plurality of bubbles may have a surface area to volume ratio of from about 8,100 to about 60,000,000 m$^2$/m$^3$, alternatively from about 8,100 to about 600,000 m$^2$/m$^3$, or alternatively from about 8,100 to about 14000 m$^2$/m$^3$. In embodiments, the smaller pore size leads to bubbles with a smaller diameter and larger surface area to volume ratio, which increases interfacial contact between the gaseous carbon dioxide and the solution of ammonia. Greater interfacial contact between the gaseous carbon dioxide and the solution of ammonia may increase rate of dissolving of the carbon dioxide within the solution of ammonia, thereby improving reaction kinetics of the carbon dioxide and the ammonia. In contrast, bubbles having a reduced surface area to volume ratio may travel through the solution of ammonia too quickly while stripping ammonia vapor from the solution of ammonia, thereby forming deposits on dry surfaces of the reactor 12 (e.g., in the headspace). The plurality of bubbles may include carbon dioxide in an amount of at least about 50 vol. %, alternatively at least about 75 vol. %, or alternatively at least about 90 vol. %, based on a total volume of the plurality of bubbles. The plurality of bubbles may include carbon dioxide in an amount of from about 50 to 100 vol. %, alternatively from about 75 to 100 vol. %, or alternatively from about 90 to 100 vol. %, based on a total volume of the plurality of bubbles. In embodiments, the carbon dioxide is pure carbon dioxide supplied as a liquid and then vaporized to a gas prior to being utilized to form the ammonium carbamate.

The method further includes the step of combining the solution of sodium hydroxide and the mixture to form the ammonium carbamate. In embodiments, the solution of sodium hydroxide is combined with the mixture at a weight ratio of sodium hydroxide to carbon dioxide of from about 0.54 to about 0.91, alternatively from about 0.64 to about 0.83, or alternatively from about 0.64 to about 0.74. In embodiments, the solution of sodium hydroxide is an aqueous solution including water.

The step of combining the solution of sodium hydroxide and the mixture is performed after the solution of ammonia reaches an NH$_3$/CO$_2$ molar ratio of from about 1.6 to about 2.1, alternatively from about 1.8 to about 2.1, or alternatively from about 2.0 to about 2.1.

The speciated solution of ammonium carbamate may include ammonium carbamate and a solvent, such as water. The speciated solution may include ammonium carbamate (formed from the ammonia and the carbon dioxide) in an amount of at least about 15 wt. %, alternatively at least about 17 wt. %, or alternatively at least about 19 wt. %, based on a total weight of the speciated solution. The speciated solution may include ammonium carbamate (formed from the ammonia and the carbon dioxide) in an amount of from about 15 to about 50 wt. %, alternatively from about 17 to about 40 wt. %, or alternatively from about 19 to about 30 wt. %, based on a total weight of the speciated solution. It is to be appreciated that the speciated solution is in equilibrium and thus the ammonium carbamate will exist at a moment in time at an amount of at least about 15 wt. % but may not at another moment in time.

The speciated solution of ammonium carbamate may have a pH of at least about 9.2, alternatively at least about 10.4, or alternatively at least about 10.6. The speciated solution may have a pH of from about 9.2 to about 11.0, alternatively from about 10.4 to about 11.0, or alternatively from about 10.6 to about 10.8. pH of the speciated solution may be utilized to determine speciation of compounds contained within the speciated solution. In embodiments, an increase in the amount of sodium hydroxide utilized to form the ammonium carbamate results in an increase in the pH of the speciated solution.

The speciated solution of ammonium carbamate may have a conductivity at 25° C. of at least about 75 mS/cm, alternatively at least about 86 mS/cm, or alternatively at least about 97 mS/cm. The speciated solution may have a conductivity at 25° C. of from about 75 mS/cm to about 160 mS/cm, alternatively from about 86 mS/cm to about 109 mS/cm, or alternatively from about 97 mS/cm to about 100 mS/cm. Conductivity of the speciated solution may also be utilized to determine speciation of compounds contained within the solution of ammonium carbamate.

The speciated solution of ammonium carbamate may have a nitrogen content of at least about 47,200 ppm, alternatively at least about 53,500 ppm, or alternatively at least about 59,700 ppm. The speciated solution may have a nitrogen content of from about 47,200 ppm to about 184,000 ppm, alternatively from about 53,500 ppm to about 147,000 ppm, or alternatively from about 59,700 ppm to about 111,000 ppm.

In certain embodiments, the method further includes the step of monitoring an amount of carbon dioxide fed through the solution of ammonia. In embodiments, data generated during monitoring of the amount of carbon dioxide fed through the solution of ammonia can be utilized to improve control of the amount of carbon dioxide fed through the solution of ammonia. The step of monitoring the amount of carbon dioxide includes one or more of the steps of determining pH of the mixture, determining conductivity of the mixture, and determining temperature of the mixture. In other embodiments, a carbon dioxide mass flow controller may be utilized to determine the amount of carbon dioxide fed through the solution of ammonia.

In one embodiment, pH is utilized to determine the amount of carbon dioxide fed through the solution of ammonia. pH measurement could be carried out with a calibrated, online pH probe submerged in the reaction mixture, or samples could be pulled from the reactor and tested with a calibrated, benchtop pH meter. As the $NH_3/CO_2$ molar ratio decreases, for example from about 3:1 to about 1.5:1, the pH of the mixture may decrease, for example, from a pH of about 10.4 at 25° C. to a pH of about 9.2 at 25° C., respectively.

In another embodiment, conductivity is utilized to determine the amount of carbon dioxide fed through the solution of ammonia. A calibrated, online conductivity probe submerged in the reaction mixture could be used to track conductivity, or a sample could be taken from the reactor and analyzed with a benchtop conductivity meter. As the $NH_3/CO_2$ molar ratio decreases, for example from about 3:1 to about 1.5:1, the conductivity of the mixture may increase, for example, from about 115 millisiemens per cm (mS/cm) at 25° C. to about 170 mS/cm at 25° C., respectively.

In yet another embodiment, an energy balance is utilized to determine the amount of carbon dioxide fed through the solution of ammonia. The reaction of carbon dioxide and ammonia is exothermic; therefore, heat generated by the reaction may be an indicator of the amount of carbon dioxide that has been reacted with the ammonia thereby indicating the $NH_3/CO_2$ molar ratio. Real-time measurement of reaction temperature, along with real-time measurement of the heat removal rate via reaction jacket and/or external heat exchanger, could be used to track the amount of carbon dioxide that has reacted with ammonia.

In certain embodiments, the method for forming ammonium carbamate may be an isothermal process. This isothermal process may proceed at a range of different temperatures, with the temperature of the mixture being maintained at a given temperature between 15° C. and 55° C., at ambient or elevated pressure, during the process. In other embodiments, the method for forming ammonium carbamate may be a semi-adiabatic process. This semi-adiabatic process may proceed with the mixture starting at a temperature as low as 15° C., and increasing to about 55° C. Heat generated during the method may be removed from the mixture utilizing a jacket or circulating the mixture through a heat exchanger. Although 55° C. is noted as a maximum operating temperature here, one skilled in the art could operate at higher temperatures and pressures while minimizing losses of $NH_3$ to the headspace of the reactor.

The system 10 for forming ammonium carbamate is also provided herein. As introduced above FIG. 1 is a flow chart illustrating a non-limiting embodiment of the system 10 for forming ammonium carbamate. The system 10 includes the reactor 12. The reactor 12 defines an interior 14. The reactor 12 includes a feed line 16 disposed within the interior 14. The feed line 16 includes an inlet 18 and an outlet 20 with the inlet 18 in fluid communication with the outlet 20. The outlet 20 is disposed within the interior 14 of the reactor 12. The system 10 further includes the solution of ammonia disposed in the interior 14. The system 10 further includes a carbon dioxide source 22 including carbon dioxide and in fluid communication with the inlet 18. The system 10 further includes a sodium hydroxide source 24 including sodium hydroxide and in fluid communication with the reactor 12. The feed line 16 is configured to receive the carbon dioxide from the carbon dioxide source 22 at the inlet 18 and release the carbon dioxide through the outlet 20. The carbon dioxide released through the outlet 20 is configured to feed through the solution of ammonia during formation of the ammonium carbamate.

The reactor 12 includes a reaction portion 26 and a headspace portion 28 adjacent the reaction portion 26 with the headspace portion 28 substantially free of ammonium carbamate and other ammonium salts during formation of the ammonium carbamate. The terminology "substantially free" as utilized herein means that the headspace portion 28 includes less than about 5 wt. %, alternatively less than about 1 wt. %, or alternatively less than about 0.1 wt. % based on a total volume (w/v %) of the headspace portion 28. As described above, bubbles or droplets including carbon dioxide and having a reduced surface area to volume ratio may travel through the solution of ammonia too quickly while stripping ammonia vapor from the solution of ammonia thereby forming deposits on dry surfaces of the reactor 12 (e.g., in the headspace). Therefore, in embodiments, formation of the ammonium carbamate within the headspace portion 28 is minimized or prevented through adequate dissolving of carbon dioxide within the solution of ammonia.

In various embodiments, the outlet 20 is submerged in the solution of ammonia during formation of the ammonium carbamate. One skilled in the art of multiphase mixing can optimize the use of agitator and/or sparger to ensure dissolution of carbon dioxide in the solution of ammonia. The outlet 20 may define a plurality of orifices and the carbon dioxide may be released through the plurality of orifices. The plurality of orifices may be configured to form the bubbles of carbon dioxide or the droplets of carbon dioxide as the carbon dioxide travels through the plurality of orifices. Each of the plurality of orifices may have a diameter of no greater than about 60 microns, alternatively no greater than about 30 microns, or alternatively no greater than about 10 microns. Each of the plurality of orifices may have a diameter of from about 1 to about 60 microns, alternatively from about 2 to about 30 microns, or alternatively from about 2 to about 10 microns.

In various embodiments, the system 10 includes a water source 32 including water, such as deionized or softened water. The system 10 may further include an ammonia source 34 including ammonia. The system 10 may further include a heat exchanger 36 for transferring heat from the reactor 12. The system 10 may further include a scrubber 38 for minimizing release of gases into the environment.

The solution of ammonium carbamate, the system for forming the same, or the method forming the same, may be utilized in a variety of applications including, but not limited to, formation of biocides and synthesis of urea.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It is understood that various changes may be made in the function and arrangement of elements described in an exemplary embodiment without departing from the scope of the disclosure as set forth in the appended claims.

EXAMPLES

Example 1: Prophetic Formulations for Exemplary Speciated Solutions of Ammonium Carbamate Prophetic Formulations for exemplary speciated solutions of ammonium carbamate may be prepared as follows. The solution of ammonia is diluted to approximately 12 wt % in a reaction vessel with cooling capabilities. Carbon dioxide is charged over time to give a final molar ratio of $NH_3/CO_2$ of about 2. Different concentrations of ammonia and NaOH can be used, and the quantity of water adjusted accordingly. Assuming a 25 wt % ammonia solution and a 50 wt % NaOH solution, 35.96-39.38 parts of water and 34.03-35.05 parts of ammonia solution are blended at ambient temperature in a vessel. This can be done with or without cooling.

Carbon dioxide is charged into mixture such that the mole ratio of ammonia to carbon dioxide is between 2.00 and 2.06 (10.99 parts is a typical charge.) Carbon dioxide reacts with ammonia in solution to form ammonium carbamate. Charging can either occur inside the vessel, or can occur in a recirculation loop of the vessel. Vessel can be run at atmospheric pressure or under pressure. Mixture is cooled while carbon dioxide is added, to keep temperature below 60° C., since the reaction gives off heat.

15.60 to 18.00 parts of 50% NaOH solution is then added slowly to the mixture to bring it to the desired pH and conductivity. The mixture is cooled during the addition of NaOH solution to keep temperature below 60° C. since the dissolution of NaOH generates heat. The prophetic formulations are provided in Table 1 below.

TABLE 1

| Ingredient | 7.8 wt % solid NaOH addition, 2.00:1 $NH_3/CO_2$ molar ratio | 8.0 wt % solid NaOH addition, 2.03:1 $NH_3/CO_2$ molar ratio | 9.0 wt % solid NaOH addition, 2.06:1 $NH_3/CO_2$ molar ratio |
|---|---|---|---|
| water | 39.38 | 38.47 | 35.96 |
| 50.0 wt % NaOH | 15.60 | 16.00 | 18.00 |
| 25.0 wt % $NH_3$ | 34.03 | 34.54 | 35.05 |
| $CO_2$ | 10.99 | 10.99 | 10.99 |

Example 2: Exemplary Speciated Solutions of Ammonium Carbamate Exhibiting Minimal Variation of Properties Over Multiple Batches Exemplary speciated solutions of ammonium carbamate (E1-E5) were prepared as follows. For each solution, a 12-liter jacketed glass vessel was fitted with a Mott Series 850 Porous Tube Assembly (part number 850-3/4-06) for sparging of carbon dioxide. The porous tube assembly has a pore size of 10 microns. Carbon dioxide was supplied by a gas cylinder, and the flow rate was controlled with a mass flow controller. 3.54 kg of 28.4 wt % aqueous ammonia solution and 4.673 kg of DI water were charged to the vessel. The reactor was sealed, except for one port that was connected to the Porous Tube Assembly and an outlet port that went to a bubbler. Carbon dioxide was sparged over a 3-hour period through the Porous Tube Assembly, with the temperature being held at about 36° C. throughout the run. After the 3-hour period, the reactor was cooled to 25° C. and 1.846 kg of 50.1 wt % sodium hydroxide solution was added, with cooling applied to maintain a temperature of 25° C. The exemplary speciated solutions of ammonium carbamate (E1-E5) were evaluated for consistency between the batches as provided in Table 2 below.

TABLE 2

|  | E1 | E2 | E3 | E4 | E5 |
|---|---|---|---|---|---|
| Conductivity (mS/cm) | 99.7 | 99.5 | 99.7 | 99.5 | 100.0 |
| pH | 10.7 | 10.7 | 10.7 | 10.7 | 10.6 |
| Total Nitrogen (ppm) | 69,000 | 70,300 | 69,300 | 68,100 | 69,600 |

After a 24-hour period, the pH was 10.7, conductivity was 99.7 mS/cm and the total nitrogen measured 69,000 ppm for E1. Similar batches (E2-E5) resulted in very low variation thereby yielding a similar product. The consistency in the total nitrogen, conductivity, and pH measurements indicate the vapor liquid equilibrium that does not remove ammonia from the solution and the full capture of carbon dioxide by the solution of ammonia.

Example 3: Comparative Solution of Ammonium Carbamate Exhibiting Formation of Solids in Headspace Portion of Reactor Due to Large Bubbles of Carbon Dioxide A comparative solution of ammonium carbamate (C1) was prepared in a 1-liter reactor in accordance with the solution of ammonium carbamate prepared in Example 1 with the exception that the pore size of the sparging element was larger, thereby forming bubbles having a smaller surface area to volume ratio (i.e., the bubbles were larger).

Figure 2:
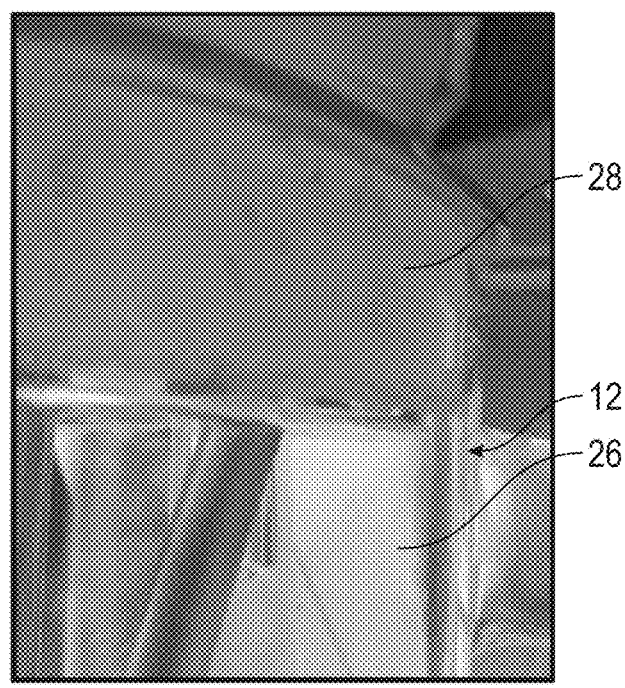
FIG. 2 is perspective view illustrating a comparative solution of ammonium carbamate.

The larger bubbles flowed through the solution of ammonia and entered the headspace prior to being fully dissolved. As shown in FIG. 2, solids including ammonium carbamate formed on the walls of the reactor within the headspace portion. The conductivity of the comparative solution of ammonium carbamate (C1) after a 24-hour period was only 94.7 mS/cm at 25° C.

Example 4: Comparative Solution of Ammonium Carbamate Exhibiting Formation of Solids in Headspace Portion of Reactor Due to Charging Headspace Portion with Carbon Dioxide A comparative solution of ammonium carbamate (C2) was prepared in a 1-liter sealed reactor in accordance with the solution of ammonium carbamate prepared in Example 1 with the exception that carbon dioxide was charged to the headspace portion of the reactor, rather than being flowed through the solution of ammonia (i.e. sparged). A solution of sodium hydroxide was then charged to the reactor.

Carbon dioxide from the headspace readily dissolved into the aqueous ammonia solution, as indicated by pressure and calorimetry measurements (not shown). However, solids including ammonium carbamate and other ammonium salts formed on the walls of the reactor within the headspace portion. The conductivity of the comparative solution of ammonium carbamate (C2) after a 24-hour period was only 88.5 mS/cm at 25° C.

Figure 3:
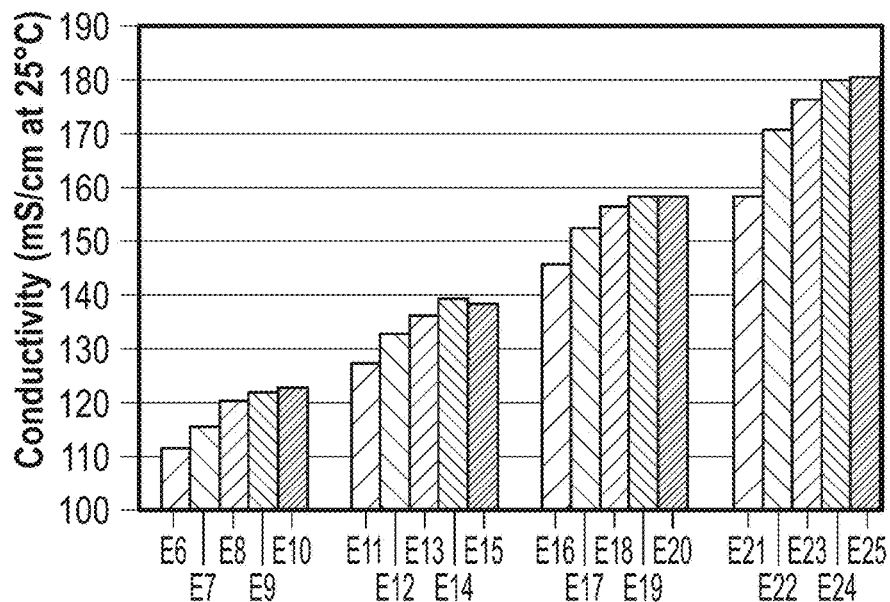
FIG. 3 is a chart illustrating experimental data of a non-limiting embodiment of the system of FIG. 1.
Figure 4:
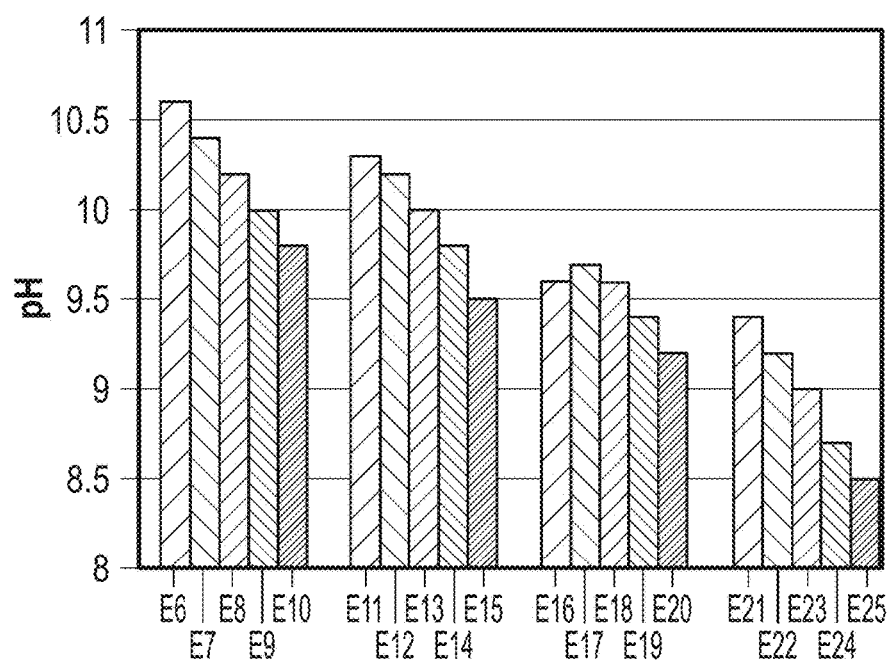
FIG. 4 is chart illustrating additional experimental data of a non-limiting embodiment of the system of FIG. 1.

Example 5: Properties of Exemplary Mixtures Formed from Solutions of Ammonia and Carbon Dioxide Exemplary mixtures (E6-E25) formed from solutions of ammonia and carbon dioxide were prepared as follows. A series of isothermal reactions were carried out, in which carbon dioxide was gradually charged through a Porous Tube Assembly into a solution of ammonia including 12.15 wt % of ammonia. pH and conductivity measurements were determined for the reaction mixtures at four different $NH_3/CO_2$ molar ratios, as provided in Table 3 and illustrated in FIG. 3 and FIG. 4. Values of conductivity and pH listed in Table 3 are for solutions after carbon dioxide has been charged into solution of ammonia, but before solution of sodium hydroxide has been added to make the final product.

TABLE 3

| | $NH_3/CO_2$ Molar Ratio | Mixture Temperature | Conductivity (mS/cm at 25° C.) | pH |
|---|---|---|---|---|
| E6 | 3:1 | 15° C. | 111.6 | 10.6 |
| E7 | 3:1 | 25° C. | 115.6 | 10.4 |
| E8 | 3:1 | 35° C. | 120.5 | 10.2 |
| E9 | 3:1 | 45° C. | 122.1 | 10 |
| E10 | 3:1 | 55° C. | 122.8 | 9.8 |
| E11 | 2.5:1 | 15° C. | 127.4 | 10.3 |
| E12 | 2.5:1 | 25° C. | 132.8 | 10.2 |
| E13 | 2.5:1 | 35° C. | 136.4 | 10 |
| E14 | 2.5:1 | 45° C. | 139.3 | 9.8 |
| E15 | 2.5:1 | 55° C. | 138.5 | 9.5 |
| E16 | 2.03:1 | 15° C. | 145.9 | 9.6 |
| E17 | 2.03:1 | 25° C. | 152.5 | 9.7 |
| E18 | 2.03:1 | 35° C. | 156.4 | 9.6 |
| E19 | 2.03:1 | 45° C. | 158.6 | 9.4 |
| E20 | 2.03:1 | 55° C. | 159.3 | 9.2 |
| E21 | 1.5:1 | 15° C. | 158.5 | 9.4 |
| E22 | 1.5:1 | 25° C. | 170.8 | 9.2 |
| E23 | 1.5:1 | 35° C. | 176.4 | 9 |
| E24 | 1.5:1 | 45° C. | 180.1 | 8.7 |
| E25 | 1.5:1 | 55° C. | 180.5 | 8.5 |

As shown in Table 3, conductivities of the exemplary mixtures increase inversely relative to the decrease in the $NH_3/CO_2$ molar ratio and the pH of the exemplary mixtures decrease relative to the decrease in the $NH_3/CO_2$ molar ratio. The data demonstrate that measurements of temperature, pH, and conductivity can be used to verify the amount of carbon dioxide charged to the reactor. Such predictable measurements are achieved due to charging $CO_2$ into the reactor as fine bubbles and preventing escape of $CO_2$ and $NH_3$ vapor from the mixture.

Example 6: Properties of Exemplary Speciated Solutions of Ammonium Carbamate

Figure 5:
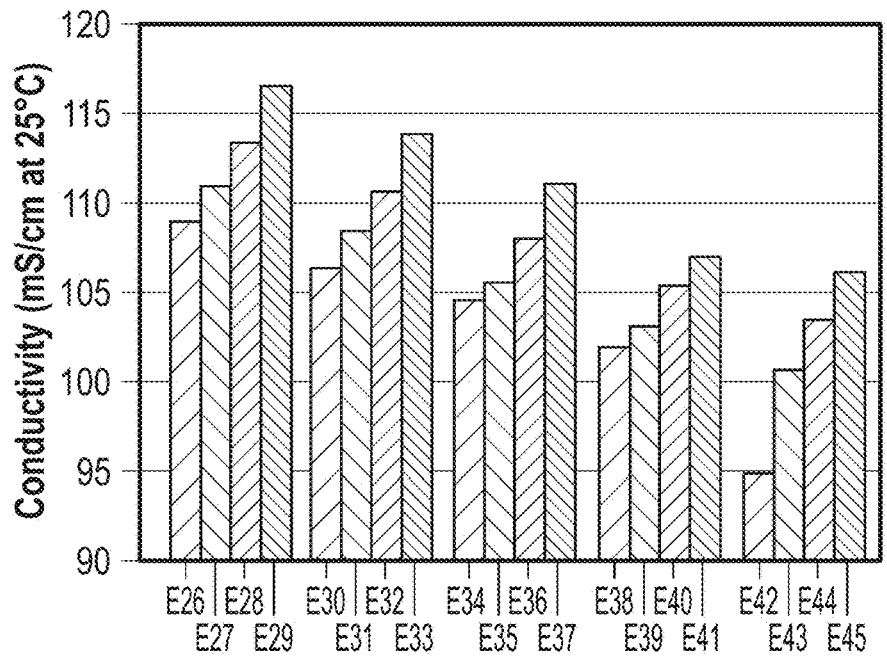
FIG. 5 is chart illustrating additional experimental data of a non-limiting embodiment of the system of FIG. 1.
Figure 6:
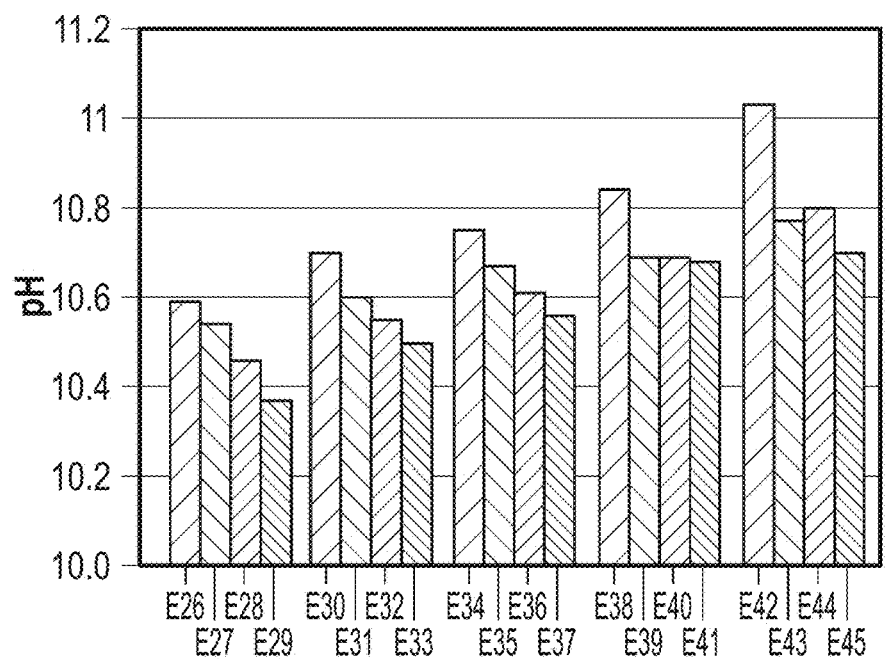
FIG. 6 is chart illustrating additional experimental data of a non-limiting embodiment of the system of FIG. 1.
Figure 7:
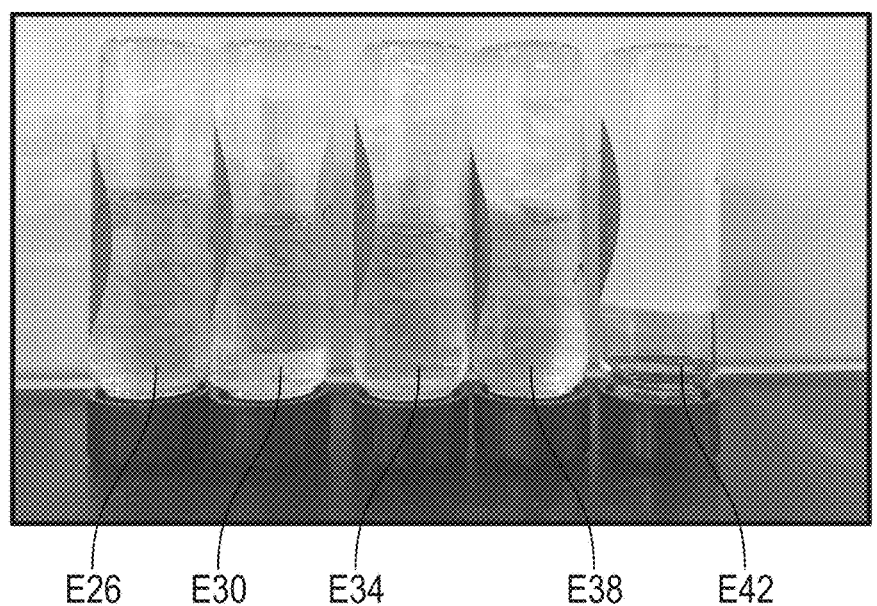
FIG. 7 is perspective view illustrating a non-limiting embodiment of solutions of ammonium carbamate of FIG. 1.

Exemplary speciated solutions of ammonium carbamate (E26-E45) were prepared as follows. A series of four reactions were carried out at 35° C., in which carbon dioxide was gradually charged through a Porous Tube Assembly into a solution of ammonia including 12.15 wt. % of ammonia. Each reaction was carried out to a different $NH_3/CO_2$ molar ratio. After charging carbon dioxide, the batch was divided into four portions, and a different level of sodium hydroxide was added to each portion, along with an appropriate amount of water to put each sample on an equal solids basis. Conductivity and pH were determined as a function of $NH_3/CO_2$ ratio and the amount of sodium hydroxide added, as provided in Table 4 and illustrated in FIGS. 5 and 6. Freezing resistance was evaluated by storing select exemplary speciated solutions of ammonium carbamate (E26, E30, E34, E38, and E42) at −10° C. for 3 days. FIG. 7 is an image of the speciated solution of ammonium carbamate after the 3 days. The vials were turned upside down before the image was captured.

TABLE 4

| | $NH_3/CO_2$ Molar Ratio | Amount of NaOH (wt. %) | Conductivity (mS/cm at 25° C.) | pH |
|---|---|---|---|---|
| E6 | 2:1 | 7 | 109 | 10.59 |
| E7 | 1.9:1 | 7 | 110.9 | 10.54 |
| E8 | 1.8:1 | 7 | 113.3 | 10.46 |
| E9 | 1.723:1 | 7 | 116.5 | 10.37 |
| E10 | 2:1 | 7.5 | 106.3 | 10.70 |
| E11 | 1.9:1 | 7.5 | 108.4 | 10.60 |
| E12 | 1.8:1 | 7.5 | 110.6 | 10.55 |
| E13 | 1.723:1 | 7.5 | 113.8 | 10.50 |
| E14 | 2:1 | 8 | 104.5 | 10.75 |
| E15 | 1.9:1 | 8 | 105.5 | 10.67 |
| E16 | 1.8:1 | 8 | 108 | 10.61 |
| E17 | 1.723:1 | 8 | 111 | 10.56 |
| E18 | 2:1 | 8.5 | 101.9 | 10.84 |
| E19 | 1.9:1 | 8.5 | 103.1 | 10.69 |
| E20 | 1.8:1 | 8.5 | 105.4 | 10.69 |
| E21 | 1.723:1 | 8.5 | 107 | 10.68 |
| E22 | 2:1 | 9 | 94.86 | 11.03 |
| E23 | 1.9:1 | 9 | 100.6 | 10.77 |
| E24 | 1.8:1 | 9 | 103.5 | 10.80 |
| E25 | 1.723:1 | 9 | 106.1 | 10.70 |

As shown in Table 4, conductivities of the exemplary speciated solutions of ammonium carbamate increase inversely relative to the decrease in the $NH_3/CO_2$ molar ratio and decrease inversely relative to the increase in the amount of NaOH. The pH of the exemplary speciated solutions of ammonium carbamate decrease relative to the decrease in the $NH_3/CO_2$ molar ratio and increase relative to the increase in the amount of NaOH. In other words, conductivities of the exemplary speciated solutions of ammonium carbamate increase as the $NH_3/CO_2$ ratio decreases, and as NaOH level decreases.

With regard to FIG. 7, exemplary speciated solutions of ammonium carbamate including 7 wt. % of NaOH exhibit improved freezing resistance as compared to exemplary speciated solutions of ammonium carbamate including 9 wt. % of NaOH.

What is claimed is:

1. A method for forming a solution of ammonium carbamate, the method comprising:
   providing a reactor comprising a solution of ammonia;
   feeding carbon dioxide through the solution of ammonia to form a mixture; and
   combining a solution of sodium hydroxide and the mixture to form ammonium carbamate.

2. The method of claim 1, wherein the step of feeding carbon dioxide is further defined as feeding a plurality of bubbles comprising gaseous carbon dioxide through the solution of ammonia to form the mixture with the plurality of bubbles comprising carbon dioxide in an amount of at least about 50 vol. % based on a total volume of the plurality of bubbles.

3. The method of claim 2 further comprising the step of forming the plurality of bubbles having a surface area to volume ratio of at least about 8,100 $m^2/m^3$.

4. The method of claim 2, wherein the plurality of bubbles comprise carbon dioxide in an amount of at least about 95 vol. % based on a total volume of the plurality of bubbles.

5. The method of claim 1 further comprising the step of monitoring an amount of carbon dioxide fed through the solution of ammonia.

6. The method of claim 5, wherein the step of monitoring the amount of carbon dioxide comprises one or more of the steps of:
   determining pH of the mixture;
   determining conductivity of the mixture; and
   determining total heat generation within the mixture.

7. The method of claim 1, wherein the solution of ammonium carbamate comprises ammonium carbamate in an amount of at least about 15 wt. % based on a total weight of the solution of ammonium carbamate.

8. The method of claim 1, wherein the solution of ammonia comprises ammonia in an amount of at least about 5 wt. %.

9. The method of claim 1 further comprising the step of combining water and the solution of ammonia prior to the step of feeding carbon dioxide.

10. The method of claim 1, wherein the carbon dioxide is fed through the solution of ammonia to an $NH_3/CO_2$ molar ratio of from about 1.6 to about 2.1.

11. The method of claim 1, wherein the solution of sodium hydroxide is combined with the mixture at a weight ratio of sodium hydroxide to carbon dioxide of from about 0.54 to about 0.91.

12. The method of claim 1, wherein:
   the solution of ammonium carbamate has a pH of at least about 9.2;
   the solution of ammonium carbamate has a conductivity of at least about 75 mS/cm;
   the solution of ammonium carbamate has a nitrogen content of at least about 47,200 ppm; or
   combinations thereof.

* * * * *